United States Patent [19]
Chun et al.

[11] Patent Number: 5,981,729
[45] Date of Patent: Nov. 9, 1999

[54] TRANSCRIPTION FACTOR GENE INDUCED BY WATER DEFICIT AND ABSCISIC ACID ISOLATED FROM *ARABIDOPSIS THALIANA*

[75] Inventors: Jong-Yoon Chun, Kwangju; Yong-Hun Lee, Seoul, both of Rep. of Korea

[73] Assignee: Korea Kumho Petrochemical Co., Ltd., Seoul, Rep. of Korea

[21] Appl. No.: 09/141,135

[22] Filed: Aug. 27, 1998

[51] Int. Cl.⁶ .............................. C12N 15/11; C12N 15/29
[52] U.S. Cl. .......................................... 536/23.6; 536/23.1
[58] Field of Search ..................................... 536/23.6, 23.1

[56] References Cited

PUBLICATIONS

Jaglo–Ottosen et al., *Science*, 280:104–106, Apr. 3, 1998.
Bray, *Trends in Plant Science*, 2:2, pp. 48–54, Feb. 1997.
Söderman et al., *The Plant Journal*, 10:2, pp. 375–381, 1996.
Shinozaki et al., *Plant Plysiol.*, 115:327–334, 1997.
Merlot et al., *Plant Physiol.*, 114:751–757, 1997.
Kishor et al., *Plant Physiol.*, 108:1387–1394, 1995.
Bohnert et al., *The Plant Cell*, 7:1099–1111, Jul. 1994.
Gehring et al., *Annu. Rev. Biochem.*, 63:487–526, 1994.
Chandler et al., *Annu. Rev. Plant Physiol. Plant Mol. Biol.*, 45:113–141, 1994.
Schena et al., *Proc. Natl. Acad. Sci. USA*, 89:3894–3898, May 1992.

*Primary Examiner*—Lynette R. F. Smith
*Assistant Examiner*—Ashwin D. Mehta
*Attorney, Agent, or Firm*—Kenyon & Kenyon

[57] ABSTRACT

This invention relates a novel gene which is induced by water deficit and abscisic acid. The gene encodes for a transcription factor, particularly homeodomain-leucine zipper transcription factor which contains a transcriptional activation domain in the C-terminal region and a DNA-binding domain in the N-terminal region. The gene can be cloned into an expression vector to produce a recombinant DNA expression system suitable for insertion into cells to form a transgenic plant transformed with this gene. The gene of this invention can be also used to produce transgenic plants which exhibit enhanced resistance to drought.

5 Claims, 8 Drawing Sheets

FIG.1

```
  1  GGCACGAGCCTTCTCTCTTAATCAAAATCAAGAAACTTACAAGATCTGGTGAAAACCATG
  1                                                             M

61  GAAGAAGGAGATTTTTTCAACTGCTGTTTCAGCGAGATTAGTAGTGGCATGACCATGAAT
  2   E  E  G  D  F  F  N  C  C  F  S  E  I  S  S  G  M  T  M  N

121  AAGAAGAAGATGAAGAAGAGCAATAACCAAAAGAGGTTTAACGAGGAACAGATCAAGTCA
 22   K  K  K  M  K  K  S  N  N  Q  K  R  F  N  E  E  Q  I  K  S

181  CTTGAGCTTATATTTGAGTCTGAGACGAGGCTTGAGCCGAGGAAGAAGGTTCAGGTAGCT
 42   L  E  L  I  F  E  S  E  T  R  L  E  P  R  K  K  V  Q  V  A

241  AGAGAGCTAGGGCTGCAACCAAGACAAATGACTATATGGTTTCAAAACAAGAGGGCTCGA
 62   R  E  L  G  L  Q  P  R  Q  M  T  I  W  F  Q  N  K  R  A  R

301  TGGAAAACTAAGCAACTTGAGAAAGAGTATAACACTCTTAGAGCCAATTACAACAATTTG
 82   W  K  T  K  Q  L  E  K  E  Y  N  T  L  R  A  N  Y  N  N  L

361  GCTTCACAATTTGAAATCATGAAGAAAGAAAAGCAATCTCTGGTCTCTGAGCTGCAGAGA
102   A  S  Q  F  E  I  M  K  K  E  K  Q  S  L  V  S  E  L  Q  R

421  CTAAACGAAGAGATGCAAAGGCCTAAAGAAGAAAAGCATCATGAGTGTTGTGGTGATCAA
122   L  N  E  E  M  Q  R  P  K  E  E  K  H  H  E  C  C  G  D  Q

481  GGACTGGCTCTAAGCAGCAGCACAGAGTCGCATAATGGAAAGAGTGAGCCAGAAGGGAGG
142   G  L  A  L  S  S  S  T  E  S  H  N  G  K  S  E  P  E  G  R

541  TTAGACCAAGGGAGTGTTCTATGTAATGATGGTGATTACAACAACAACATTAAAACAGAG
162   L  D  Q  G  S  V  L  C  N  D  G  D  Y  N  N  N  I  K  T  E

601  TATTTTAGGGTCCAGGGAGAGACTGATCATGAGCTGATGAACATTGTGGAGAAAGCTGAT
182   Y  F  R  V  Q  G  E  T  D  H  E  L  M  N  I  V  E  K  A  D

661  GATAGTTGCTTGACATCTTCTGAGAATTGGGGAGGTTTCAATTCTGATTCTCTCTTAGAC
202   D  S  C  L  T  S  S  E  N  W  G  G  F  N  S  D  S  L  L  D

721  CAATCTAGCAGCAATTACCCTAACTGGTGGGAGTTTTGGTCATAAAAGCATATAAGAAAA
242   Q  S  S  S  N  Y  P  N  W  W  E  F  W  S  *

781  AAACAGAACATAAGCGAAGAGAAAGAGTGTGAATAGTTTGTAAATTATGTGTTAAGAAAA
841  TAAATTTAGTTTAGTTTAAATCTTGTTTCGATCTATGTATCTACTATGTTCAATACTCTT
901  TGTAGCTAATTAGTAGCTTATAATGAGACTAGAAAAGTTTTGAAGTCAAAAAAAAAAAAA
961  AAAAA
```

FIG. 2

A. Homeodomain

```
                  helix 1      loop     helix 2  turn     helix 3
             *          *          *              *    ****  *
Athb-12  KKSNNQKRFNEEQIKSLELIFESETRLEPRKKVQVARELGLQPRQMTIWFQNKRARWKTKQ    100
Athb-7   HNK---R----D-----MM---------------L----------VA-----------S---   82
Athb-6   GL-EKKR-L-IN-V-A--KN--L-NK---ER--KL-Q--------VAV-----R--------   59
CHB6     QI-EKKR-LSIN-V-A--KN--V-NK---ER--KL-Q--------VAV-----R--------   57
CHB3     QQPEKKR-LKAD--QF--KS--TDNK---E----L-K--------VA------R-----T--   57
Athb-5   TAAEKKR-LGV--V-A--KN--IDNK---ER--KL-Q--------VA------R--------   57
CHB1     HPPEKKR-LTVD-V-Y--KS--VENK---DR--L-KD--------VA------R---Y----   54
CHB4     SGGSKKR-LNM--VRT--KS--MGNK---DR-LEL--A-------IA------R--------   54
Athb-1   QLPEKKR-LTT--VHL--KS--TNKN---ER-T-L-KK-------VAV-----R--------   52
```

B. Leucine zipper motif

```
Athb-12  | L EKEYNT L RANYNN L ASQFEI M KKEKQS L VSELQR L |   100
Athb-7   | - -T---I - -Q--D- - -----S L -----A - -LQ-ISK - |    80
Athb-6   | - -----GD - KTQ-DS - RHN-DS L RRDNE- - LK-IRE  - |    36
CHB6     | - -RD-GV - K----DS - KLKNDT L QQ-N--  - KA-VLD - |    39
CHB3     | - --D-DV - QNS--S  - KADYDN L LA--EK  - LGQIKE - |    36
Athb-5   | - -RD-GV - KS-FDA  - KRNRDS L QRDND-  - RL-VIL D |    25
CHB1     | - --D-DS - KEC-DK  - RDDHDR L S--NEK  - HAQIMA - |    31
CHB4     | - --D-DL - KSQFDA V KAENDS L QSHN-K  - R--VTS  - |    22
Athb-1   | - -RD-DL - KST-DQ  - L-NYDS L VMDNDK  -         |    31
```

FIG.4A ← Athb-12

FIG.4B — 25S / 18S (Lanes: 1. Seedling, 2. Root, 3. Stem, 4. Leaf, 5. Flower)

FIG.5A ← Athb-12

FIG.5B ← Athb-7

FIG.5C — 25S / 18S (Lanes: C, D1, D2, D3, D4 — Drought)

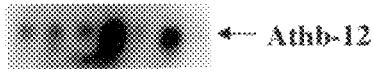
FIG.6A ← Athb-12
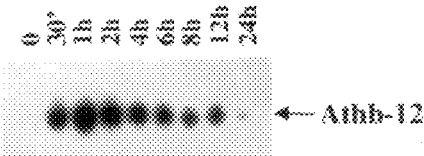
FIG.7A ← Athb-12
FIG.6B — 25S — 18S
FIG.7B ← Athb-7
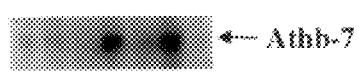
FIG.6C ← Athb-7
FIG.6D — 25S — 18S
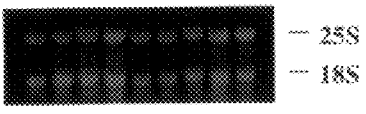
FIG.7C — 25S — 18S

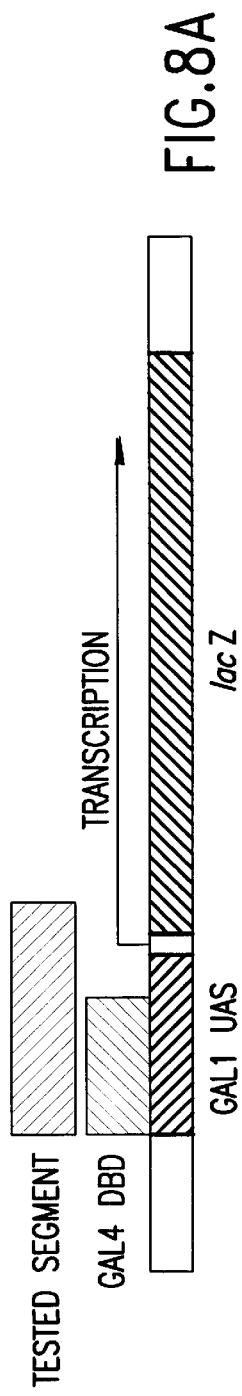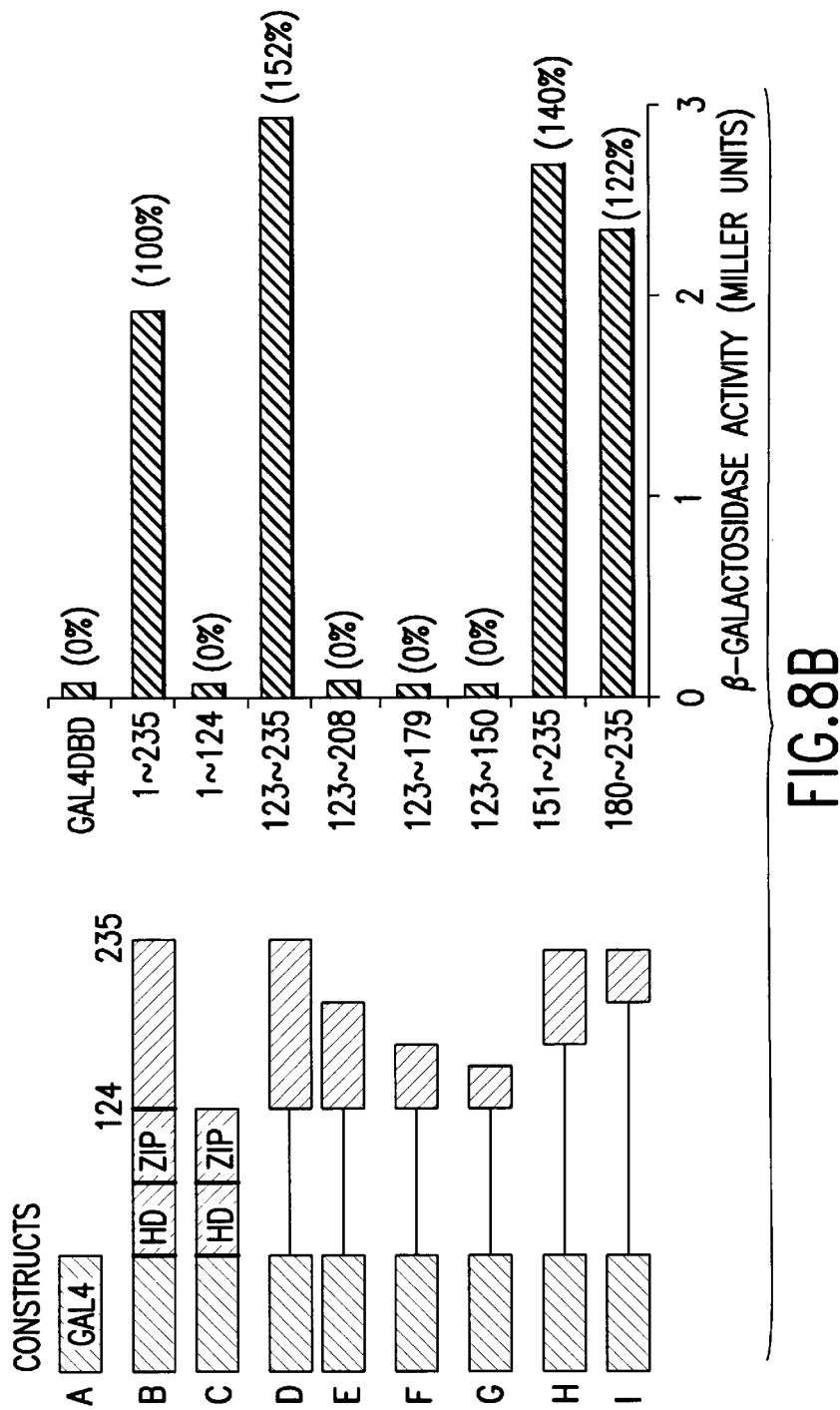

FIG.8C
(Constructs)
| a | b | c |
|---|---|---|
| d | e | f |
| g | h | i |
(Trp-)
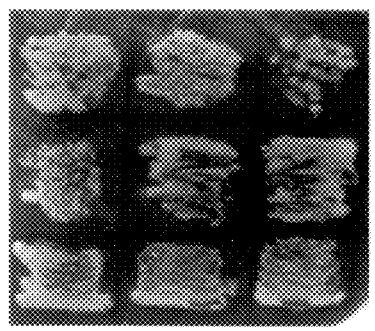
(His-)
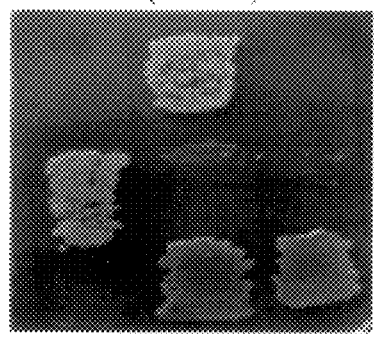
(LacZ)
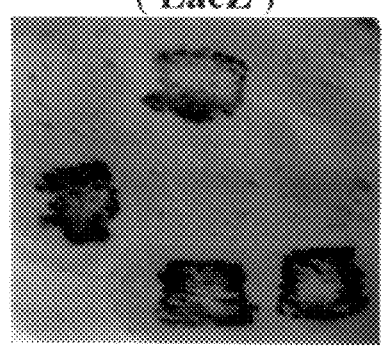

TRANSCRIPTION FACTOR GENE INDUCED BY WATER DEFICIT AND ABSCISIC ACID ISOLATED FROM *ARABIDOPSIS THALIANA*

BACKGROUND OF THE INVENTION

Water deficit is one of the major limiting factors for plant productivity and plant distribution (Boyer 1982). Plants respond to drought by modifying their morphological, physiological and metabolic processes (McCue and Hanson 1990). Depending on the efficiency of the response, plant species can withstand longer or shorter periods of water deficit. Some responses may result from cell damage while others may correspond to adaptive processes (Bray 1997). Plant adaptive responses to water stress are accompanied by the accumulation of specific mRNAs (Shinozaki and Yamaguchi-Shinozaki 1997). In addition, the mRNAs of water-stress-inducible genes decrease when the plants are released from stress conditions, which is consistent with evidence that shows that these genes respond to water stress. It is believed that the altered phenotype of plants with an enhanced ability to survive and grow under environmental stresses is largely the result of changes in gene expression (Ingram and Bartels 1996; Shinozaki and Yamaguchi-Shinozaki 1997). Most of the genes that respond to drought are also induced by exogenous application of abscisic acid (ABA) (Merlot and Giraudat 1997; Bray et al. 1997). It has been well documented that ABA has important roles in the tolerance of plants to drought. For example, applied ABA inhibit stomatal opening and promotes stomatal closure (Blatt and Thiel 1993; Ward et al. 1995). It appears that water stress triggers the production of ABA, which in turn induces various genes. A number of genes that respond to drought and exogenous ABA at the transcriptional level have been recently isolated and characterized from several species (for review, see Ingram and Bartels 1996; Bray 1997; Shinozaki and Yamaguchi-Shinozaki 1997). The functions of these gene products are thought to have a role in protecting the cells from water deficit (Ingram and Bartels 1996; Bray 1997).

The homeobox genes are characterized by a conserved 180-bp nucleotide sequence known as the homeobox, which encodes a 60-amino acid DNA binding homeodomain (HD) structured in three α-helices (Gehring et al. 1994). This DNA binding property indicates that homeodomain proteins function as transcription factors in controlling downstream target genes. The HD factors controls several developmental decisions in animals, apparently acting as molecular switches to control the fates of the cells during development (reviewed in McGinnis and Krumlauf 1992; De Robertis 1994). In higher plants, a class of the HD genes was first discovered in *Arabidopsis thaliana* (Ruberti et al. 1991). Unlike other classic homeobox proteins, the products of these genes contain a second element that codes for a putative leucine zipper motif, which is closely linked to the carboxy-terminal region of the HD. So far, these termed homeodomain-leucine zipper (HD-Zip) proteins have been identified only in plants such as sunflower (Chan et al. 1994), carrot (Kawahara et al. 1995), soybean (Moon et al. 1996), tomato (Meissner and Theres 1995), rice (Meijer et al. 19970 and Arabidopsis (Mattsson et al. 1992; Söderman et al. 1994; Lee and Chun 1998). The uniqueness of the HD-Zip proteins in plants suggests that these HD-Zip proteins function as a mediator of plant development; for example, coupling of the developmental response to an environmental signal (Schena and Davis 1992). Several lines of evidence support this notion.

We have recently isolated a novel homeobox-containing gene, Athb-12, which was induced by water deficit and exogenous ABA treatment (Lee and Chun 1998). The yeast genetic study revealed that the Athb-12 protein contains a transcriptional activation domain in the C-terminal region. In addition, this protein was found to bind to the 12 bp palindromic sequence EN (TCAATTAATTGA), which is the consensus recognition site determined for Drosophila Engrailed and a number of other animal HD proteins (Desplan et al. 1988). These data indicate that the Athb-12 is a transcription factor involved in the regulation of the plant's response to water deficit. Generally, transcription factors regulate multiple target genes. Thus, the overexpression of Athb-12 in plants may increase the resistance to drought. Recently, increased expression of Arabidopsis CBF1, a transcription factor that binds to the CRT/DRE sequence, induced COR (cold-regulated) genes and increased the freezing tolerance of Arabidopsis plants (Jaglo-Ottosen et al. 1998).

SUMMARY OF THE INVENTION

This invention relates a novel gene which is induced by water deficit and abscisic acid. The gene was identified to encode for a transcription factor, particularly homeodomain-leucine zipper transcription factor which has a transcriptional activation domain in the C-terminal region and a DNA-binding domain in the N-terminal region. The gene can be cloned into an expression vector to produce a recombinant DNA expression system suitable for insertion into cells to form a transgenic plant transformed with this gene. The gene of this invention can be also used to produce transgenic plants which exhibit enhanced resistance to drought. Due to the properties of the drought- and ABA-inducible gene as a transcription factor, the overexpression of the gene in plants may increase the resistance to drought.

BRIEF DESCRIPTION OF THE DRAWINGS

FIG. 1. Nucleotide and predicted amino acid sequences of the *Arabidopsis thaliana* cDNA clone encoding Athb-12. The homeodomain is underlined from amino acid 26–86, and the leucine and methionine in the proposed leucine-zipper motif are highlighted in black. The asterisk represents the termination codon. The putative polyadenylation signal is shown in bold-face type.

FIGS. 2A and 2B. Comparison of the amino acid sequence of the homeodomain and leucine zipper motif of Athb-12 with the corresponding domains of the HD-Zip family members; Athb-5,-6, -7 (Söderman et al. 1994), CHB1, 3, 4, 6 (Kawahara et al. 1995) and Athb-1 (Ruberti et al. 1991). Dashes indicate identical amino acids between Athb-12 and other sequences. The highly conserved residues and the four invariant residues in all homeodomains are marked by asterisks(A). The conserved leucine residues in the leucine zipper motif are boxed(B).

FIGS. 4A and 4B. Northern blot analysis of Athb-12 mRNA expression in Arabidopsis thaliana. Total RNA samples of Arabidopsis thaliana seedling (3-day old)(1), root(2), stem(3), leaf(4) and flower(5) were isolated using RNeasy Plant Total RNA Isolation Kit (QIAGEN). Each lane contains 10 μg of total RNA. The position of Athb-12 (0.96 kb) is indicated (arrow)(A), as are the positions of the ethidium-stained rRNAs(25S and 18S)(B).

FIGS. 5A–5C. Northern blots showing the effect of water-stress on the accumulation of Athb-12 MRNA. Each lane contains 10 μg of total RNA from Arabidopsis thaliana plants raised under standard growth conditions for 14 days and then treated with water-stress. (A) RNAs from control plants or plants harvested 1 (D1), 2 (D2), 3(D3), and 4 (D4) days after exposure to water-stress were probed with the 3'-specific probe of Athb-12 cDNA. (B) Blot A was reprobed with a 3'-specific probe of Athb-7 after removing the Athb-12 probe. The Athb-7 cDNA fragment, which does not contain homeodomain and leucine zipper motifs, was amplified by using the Athb-7-specific primers (5' primer, 5'-AAAGAGGCGACGCAAAAGAAGA-3' and 3' primer, 5'-CTACTTAGCTACAAAGCATGACGAG-3'. The PCR products were subcloned into pGEM-T vector (Promega) and verified by sequencing analysis. The positions of the Athb-12 (0.96 kb) and Athb-7 (1.17 kb) are indicated (arrow). (C) The photograph of ethidium bromide-stained rRNAs (25S and 18S).

FIGS. 6A–6D. Northern blot analysis showing the effect of exogenously applied plant hormones on the accumulation of Athb-12 and Athb-7 mRNAs. (A) The blot was hybridized with the 3'-specific probe of Athb-12 cDNA. (C) The blot was hybridized with the 3'-specific probe of Athb-7 cDNA. The positions of the Athb-12 and Athb-7 are indicated (arrow). (B) and (D); The photographs of ethidium bromide-stained rRNAs (25S and 18S).

FIGS. 7A–7C. The time courses of accumulation of the Athb-12 and Athb-7 mRNAs in response to ABA. (A) The blot was hybridized with the 3'-specific probe of Athb-12 cDNA. (B) The blot in (A) was reprobed with a 3'-specific probe of Athb-7 after removing the Athb-12 probe. The positions of the Athb-12 and Athb-7 are indicated (arrow). (C) The photograph of ethidium bromide-stained rRNAs (25S and 18S).

FIG. 8. Localization of transcriptional activation domain in Athb-12 in a yeast genetic system. (A) Schematic diagram of yeast one hybrid assay for transcriptional activation domain study. (B) β-Galactosidase activity of each construct was measured using the vector pGBT9 (GAL4DBD) transformant as a blank, and the value obtained for the DBD-Athb-12 fusion was set at 100%. The activity obtained with each of the other constructs is reported as a percentage of this activity. The results shown are the means of 5 to 10 independent transformations. HD, homeodomain; Zip, leucine zipper, DBD, DNA-binding domain. (C) Transformants were grown under lacking Trytophan (Trp-) or Histidine (His-) and also assayed for their β-galactosidase activity (LacZ).

DETAILED DESCRIPTION OF THE INVENTION

Figure 3A:
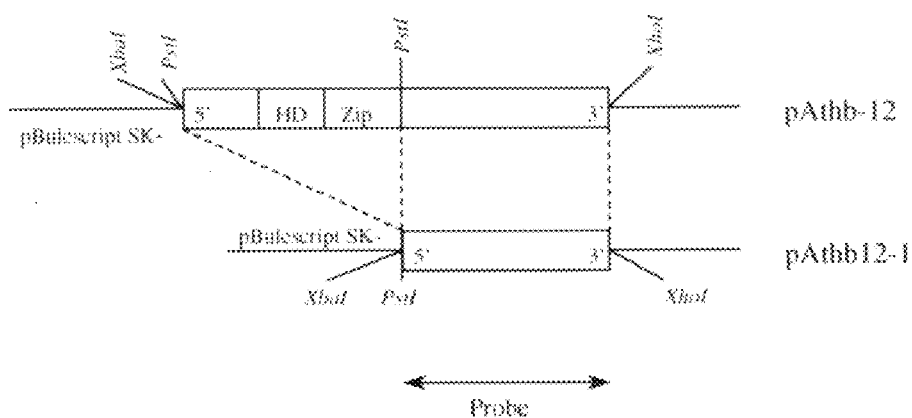
FIGS. 3A and 3B. Southern blot analysis of *Arabidopsis thaliana* genomic DNA. (A) Schematic diagram of Athb-12 cDNA clone, pAthb-12, and a subclone of 3'-end fragment of the Athb-12 cDNA, pAthb12-1, showing restriction sites and the probe used for the genomic DNA analysis and the Northern blot analysis. Homeodomain and leucine zipper motif are marked by HD and Zip, respectively. (B) DNA gel blot hybridization analysis. Arabidopsis genomic DNA(10 μg) was digested with HindIII (H) or PstI (P). After separation in a 1.0% agarose gel, the digested DNA was transferred onto a nylon membrane and hybridized with the $^{32}$P-labeled 3'-end of Athb-12 cDNA which excluded the homeodomain and leucine zipper region. The size of DNA markers are indicated on the left side.

The present applicant has identified a homeobox-containing cDNA clone, referred to Athb-12. This cDNA was identified by screening an Arabidopsis thaliana whole plant cDNA library for homeobox-containing sequences using a polymerase chain reaction (PCR) cloning strategy. The full-length cDNA encodes a protein of 235 amino acids. It contains the conserved DNA binding domain and the leucine-zipper motif, characteristic of the homeodomain-leucine zipper family of transcription factors. Yeast genetic study localized the transcriptional activation domain of Athb-12 in the C-terimal region. This protein was found to bind to the 12 bp palindromic sequence EN (TCAATTAATTGA), which is the consensus recognition site determined for Drosophila Engrailed and a number of other animal HD proteins (Desplan et al. 1988). RNA analysis identified only one 0.96 kb transcript, consistent with the size of Athb-12 cDNA. The Athb-12 transcript was detected in stem, leaf, flower and root as well as seedling. Treatment of water-stress (drought) and exogenous abscisic acid resulted in the accumulation of Athb-12 mRNA. In addition, the time course analysis of the Athb-12 response to ABA showed that the Athb-12 mRNA is induced within 30 min after exogenous ABA treatment. Based on the results that the Athb-12 gene is induced by water deficit and ABA, and encodes for a homeodomain-leucine zipper transcription factor containing a transcriptional activation domain in the C-terminal region and a DNA binding domain in the N-terminal region, we assume that Athb-12 plays an important role in the regulation of the plant's response to water deficit. Generally, transcription factors regulate multiple target genes. Thus, the overexpression of Athb-12 in plants may increase the resistance to drought. The gene can be cloned into an expression vector to produce a recombinant DNA expression system suitable for insertion into cells to form a transgenic plant transformed with this gene. The gene of this invention can be also used to produce transgenic plants which exhibit enhanced resistance to drought.

Materials and Methods
Plant Materials and Growth Conditions

Seeds of Arabidopsis thaliana (Columbia ecotype) were kindly provided by Dr. Hyeon-Sook Cheong (Department of Genetic Engineering, Chosun University). Seeds were surface-sterilized in a 70% ethanol for 15 s and then in 10% chlorox solution for 10 min, followed by at least five rinses in sterile distilled water. For drought treatments, the seeds were plated on 30 ml solidified 0.8% agar plates containing 0.5× MS medium (Murashige and Skoog 1962) supplemented with 1.5% sucrose. They were then grown in a culture room at 25° C. with a 16 h photoperiod for 14 days before treatment. For hormone treatments, the sterilized seeds were placed in 50 ml liquid MS medium supplemented with 1.5% sucrose and grown on a rotary platform for 14 days before hormone treatment. Treatments with hormones were performed by addition of the plant hormones abscisic acid (ABA), gibberellic acid (GA3), indole-3-acetic acid (IAA), kinetin or a combination of ABA+GA3 or IAA+kinetin to liquid cultures to the final concentration of 10 μM. Samples were harvested after treatment for 72 h. For the time courses of accumulation of the Athb-12 and Athb-7 mRNAs in response to ABA, Arabidopsis seedlings were grown in liquid cultures for 14 days and treated with ABA at the final concentration of 10 μM and then harvested at a variety of times(0 min, 30 min, 1 h, 2 h, 4 h, 6 h, 8 h, 12 h, and 24 h).

PCR Amplification of Homeobox-containing cDNA Fragments

The Arabidopsis thaliana cDNA library (Stratagene, La jolla, Calif., USA) was used as a template for the amplification of homeobox sequences by PCR. The universal T3 primer was used as a 5' primer (forward) for the PCR. A degenerate oligonucleotide, 5'-TTCTGAACCA(G/A/T)AT(A/C)G(C/T)(A/C)A (C/T)(C/T)TG-3', complementary to the sequences encoding the highly conserved homeodomain helix three was designed based on a comparative analysis of 15 different plant homeodomain DNA sequences selected from GenBank and EMBL databases and used as a 3' primer (reverse). The PCR reaction mixture contained 10 mM Tris-HCl pH 8.3, 50 mM KCl, 1.5 mM $MgCl_2$, 200 μM dNTP, 1 μM of each primer, 2.5 units of Taq DNA polymerase (Promega, Madison, USA) and 2 μl cDNA library suspension containing about $10^8$ plaque-forming bacteriophage in a final 50 μl volume. The reaction mixture was heated to 94° C. for 5 min, followed by 40 cycles of amplification at 94° C. for 1 min, 58° C. for 1 min, and 72° C. for 1 min. After the last amplification cycle the samples were incubated at 72° C. for 5 min. These PCR products were cloned into the pGEM-T vector (Promega). Inserts of the resulting transformants were sequenced and those containing homeobox sequences were identified using the BLAST family of programs (Benson et al., 1997). The Arabidopsis cDNA library was screened to isolate full-length cDNA clones using the PCR-amplified cDNA fragment as a probe.

Isolation of the Psx Clone

Arabidopsis thaliana whole plant cDNA library ($1 \times 10^6$ plaques) was plated at the density of $5 \times 10^4$ plaques per plate. A nylon membrane (Hybond-N, Amersham International, Buckinghamshire, UK) was lifted and screened with the labeled 0.4 kb PCR product. The probe was labeled with [α-$^{32}$P]dCTP using the random labeling kit (Boehringer Mannheim, Mannheim, Germany). The filters were pre-hybridized in a buffer containing 5× SSPE, 5× Denhardt's solution, 0.1% SDS and 0.2 mg/ml denatured salmon sperm DNA for 2 h at 55° C. Hybridization was carried out overnight at 55° C. in the same solution containing the probe. Filters were washed at 55° C. as follows: two times for 10 min each at 2× SSC/0.1% SDS; once at 1× SSC/0.1% SDS for 10 min; two times for 10 min each at 0.1× SSC/0.1% SDS. X-ray films were exposed to the filters between the intensifying screens. Positive clones hybridized to the probe were recovered as phagemid plasmids by in vivo excision (ZAP Express cloning kit, Stratagene) according to the manufacturer's protocol.

DNA Sequencing Analysis

Subcloned PCR products and cDNA clones were sequenced either manually with the Sequenase II kit (Amersham/United States Biochemical) or with an ALFexpress DNA Sequencer (Pharmacia Biotech) using Taq or T7 DNA polymerase and fluorescent carbocyanine dye (Cy5) (Pharmacia Biotech). Computer-assisted sequence analysis was done with the DNASIS program (Hitachi Software, San Bruno, Calif.).

Preparation of Genomic DNA and Southern Blot Analysis

Genomic DNA was prepared from Arabidopsis thaliana whole plants according to Sambrook et al. (1989). Ten micrograms of genomic DNA was digested was digested with HindIII (H) or PstI (P). After separation in a 1.0% agarose gel, the digested DNA was transferred onto a nylon membrane. To avoid cross-hybridization, the 3' end 550 bp fragment of Athb-12 cDNA which does not contain the homeodomain and leucine zipper motif region was used as a probe in the Southern blot. The 550 bp fragment was subcloned into pBluescript SK- by removing the 5' end 410 bp PstI fragment from the cDNA clone, pAthb-12, and self-ligating the plasmid, resulting in plasmid pAthb12-1. The fragment was labeled with [α-$^{32}$P] dCTP using the random labeling kit (Boeringer Mannheim). Hybridization was done at 55° C. in QuikHyb solution as recommended by the manufacturer (Stratagene). After hybridization overnight, the DNA filters were washed as described for the cDNA library screening.

Preparation of RNA and Northern Blot Analysis

Total RNA samples of Arabidopsis thaliana were isolated using RNeasy Plant Total RNA Isolation Kit (QIAGEN). RNA was denatured in 1× MOPS buffer (20 mM MOPS, 8 mM sodium acetate, 1 mM EDTA), 50% (v/v) deionized formamide and 2.2 M formaldehyde at 65° C. for 15 min and fractionated by electrophoresis on a 1% agarose gel containing 2.2 M formaldehyde and 1× MOPS buffer. RNA was capillary-blotted in 10× SSC on a Hybond-N membrane (Amersham). The filter was prehybridized in QuikHyb solution (Stratagene) containing 0.2 mg/ml salmon sperm DNA at 55° C. for 1 h. The probe used was the radiolabeled 550 bp XbaI-XhoI fragment of the 3' end of Athb-12 cDNA, which does not contain homeodomain and leucine zipper motifs. Hybridization was carried out at 55 ° C. After hybridization overnight, the RNA filters were washed as described for the cDNA library screening in the text.

Transcription Activation Assay

GAL4 fusion Athb-12 domains for yeast genetic assays were constructed by subcloning various Athb-12 domain-derived sequences into the vector pGBT9, which is known as the GAL4 DNA-binding domain. A variety of deletion domains of Athb-12 were generated by PCR amplification and subcloned into the BamHI and EcoRI sites of the pGBT9 vector in-frame as following: full-length of Athb-12 protein (amino acids 1 to 235), N-terminal domain containing the homeodomain and leucine-zipper motif (amino acids 1 to 124), C-terminal domain (amino acids 123 to 235), and a series of deletion in the C-terminal domain (amino acids 123 to 208, amino acids 123 to 179, amino acids 123 to 150, amino acids 151 to 235 and amino acids 180 to 235). S. cerevisiae HF7C was transformed with pGBT9(as a negative control) and above constructs, and grown for 2days on SD-Trp plates. The transcription activation functions of the individual colonies were confirmed by the tests of the growth ability on SD-His plates and also by the assays of β-galactosidase activity. The results are made by the means of dual determinations from 3 to 5 individual transformations.

The quantitative assay of β-galactosidase activity was performed as described in the Clontech protocol, with a minor modification: 1.5 ml of overnight transformed yeast culture (OD600, ~1.0) was collected by centrifugation, resuspended in 300 μl of Z buffer, aliquot 100 μl to fresh microtube, frozen in liquid nitrogen and thawed at 37° C. for 1 min. After that, add 0.7 ml of Z buffer and 0.16 ml of ONPG(4 mg/ml in Z buffer). The reactions were allowed to proceed until the mixtures are turned to yellow and then stopped by the addition of 0.4 ml of 1M $Na_2CO_3$. Cell debris was removed by centrifugation in a microfuge for 10 min, and the absorbance of the supernatant was measured at 420 nm. For each construct, three independent transformants were assayed.

Gel Shift Assay

The Athb-12 cDNA corresponding to the full-length of Athb-12 protein (amino acids 1 to 235) was subcloned into the EcoRI and BamHI sites of the expression vector pRSETA( ). This construct DNA (1 μg) was used to generate the extracts containing full-length Athb-12 protein by coupled in-vitro transcription/translation, using Promega's TNT Coupled Reticulocyte Lysate System. The 2 μl of the in vitro translation product was used for gel shift assay. The following oligonucleotides were synthesized for use in the gel shift assay:

HD; 5'-NAATNATTN-3
EN; 5'-TCAATTAATTGA-3
AH1; 5'-CAATWATTG-3 (W=A or T)
AH2; 5'-CAATSATTG-3 (S=G or C)

Double stands were prepared by annealing each oligonucleotide in buffer (final concentration: 25 mM Tris-HCl, pH 8.0, 5 mM MgCl$_2$ and 25 mM NaCl), heating to 70° C. for 10 min and cooling to room temperature. The double stranded DNA (50 pmole) was 5' end-labeled with [γ-32P] ATP and T4 polynucleotide kinase. Binding was carried out for 30 min at room temperature in 30 μl containing: 25 mM HEPES, pH7.6, 1 mM MgCl$_2$, 1 mM DTT, 0.5 mM EDTA, 10% glycerol and 2 μl of in vitro translation product. Each reaction received 20,000 cpm oligonucleotide (0.1–0.5 ng) and was incubated an additional 30 min at room temperature. Samples were electrophoresed on non-reducing polyacrylamide gels in a high ionic strength buffer (0.38 M glycine, 50 mM Tris, 2.1 mM EDTA, pH 8.5). Gels were dried, followed by exposure to x-ray film at –70° C. with an intensifying screen.

Results

Isolation of cDNA Clones for Athb-12

To find new homeobox genes from *Arabidopsis thaliana*, PCR was used to isolate the segments of cDNAs containing homeobox sequences using the *Arabidopsis thaliana* cDNA library (Stratagene, La jolla, Calif., USA) as a template. A 0.4 kb PCR product was obtained by PCR-based screening. Nucleotide sequence analysis showed that the 0.4 kb clone contained a novel homeobox sequence. This clone was subsequently used for screening the Arabidopsis cDNA library to obtain full length cDNAs. One positive clone hybridized to the 0.4 kb probe was identified and fully sequenced on both strands. The cDNA is a 965 bp with a major open reading frame predicted to encode a 235 amino acid polypeptide with a molecular mass of 27551 Da (FIG. 1 (SEQ. ID No. 1)). The nucleotide sequence around the first ATG codon AACCATGGA (position 54–62) strongly matches the proposed plant translation initiation motif, AACAAUGGC (Lücke et al. 1987). In addition, the presence of an in-frame TAA stop codon located 37 bp upstream of the 235 amino acid open reading frame suggests that the cDNA is full-length. The open reading frame is followed by 200 bp untranslated region terminating in a poly(A) tail. A putative polyadenylation signal sequence (AATAAA) (Joshi 1987) is present in the 103 bp 5' end of the poly(A) tail.

Sequence Analysis

Computer-assisted search through NCBI data bases revealed that the deduced protein sequence of Athb-12 contains a homeodomain (amino acids 26–86) and a leucine zipper motif (amino acids 87–122) (FIG. 2 ((SEQ. ID No. 2)). When compared to the available HD-Zip family protein sequences, the Athb-12 protein shares the highest homology with Athb-7 protein; 82%, 93% and 80%, 89% (identity followed by similarity) in homeodomain and leucine zipper motif, respectively (FIG. 2). We therefore propose that these genes are members of a related gene family. Several related HD-Zip family genes have been identified from Arabidopsis. Arabidopsis Athb-2 and Athb-4 genes, which have a high amino acid identity (89%) in the HD-Zip motif region, seem to regulate morphological adaptations to changes in light quality (Carabelli et al. 1993). Also, two other related genes, Arabidopsis KNAT1 and KNAT2, which encode proteins with 80% amino acid identity in the homeodomain, may play a role in leaf morphogenesis (Lincoln et al. 1994). Outside the homeodomain and leucine zipper motif, the homology between Athb-12 and Athb-7 proteins is significantly lower.

FIG. 2 shows the alignment of the homeodomain and leucine zipper motif of Athb-12 with the corresponding amino acid sequences of the published plant sequences. The amino acid sequences of the HDs are more similar to each other than to the leucine zipper motifs. This feature has also been usually observed in other HD-Zip family proteins. All of these proteins showing a high homology to Athb-12 belong to the class I HD-Zip family. Based on the sequence homology, the HD-Zip proteins have been tentatively grouped in four different families, named HD-Zip I, II, III and IV (Sessa et al. 1994; Meijer et al. 1997). The homeodomain in Athb-12 possesses the four invariant amino acid residues found in all the homeodomains of higher eukaryotes (Scott et al. 1989) as well as five out of the eight highly conserved residues (Gehring et al. 1990).

The leucine zipper motif lies adjacent to the C-terminal side of the homeodomain of Athb-12. The leucine zipper motif is known to form an amphipathic α-helix with a series of leucine residues spaced by exactly seven amino acid residues and to be responsible for dimerization to juxtapose a pair of target DNA contacting surface (Busch and Sassone-Corsi 1990). Recently, it has been shown that the HD-Zip family proteins Athb-1 and Athb-2 recognize dyad-symmetric DNA sequences as homodimers formed via dimerization of the leucine zipper (Sessa et al. 1993). Therefore, the presence of a homeodomain and a leucine zipper motif in the Athb-12 suggests that Athb-12 encodes a DNA-binding protein which may also exist as a dimer.

Southern Blot Analysis

Figure 3B:
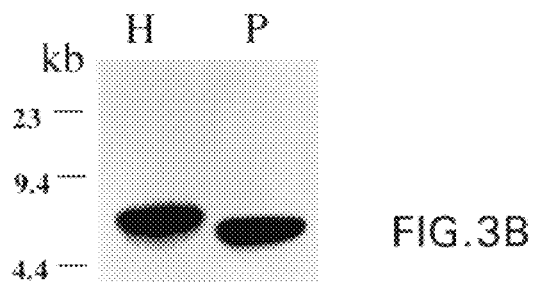

Southern blot analysis was used to examine the number of genes encoding Athb-12 in Arabidopsis. To avoid cross-hybridization, the 3' end 550 bp fragment of Athb-12 cDNA which does not contain the homeodomain and leucine zipper motif region was used as a probe in the Southern blot. The 550 bp fragment was subcloned into pBluescript SK- by removing the 5' end 410 bp PstI fragment from the cDNA clone, pAthb-12, and self-ligating the plasmid, resulting in plasmid pAthb12-1 (FIG. 3A). The fragment was labeled with [α-$^{32}$p] dCTP using the random labeling kit (Boeringer Mannheim). Hybridization was done at 55 ° C. in QuikHyb solution as recommended by the manufacturer (Stratagene). After hybridization overnight, the DNA filters were washed as described for the cDNA library screening. Each digestion with the restriction enzymes produced a single signal (FIG. 3B), suggesting that Athb-12 gene is a single copy in *Arabidopsis thaliana*.

Northern Blot Analysis

To determine the expression pattern and size of Athb-12 transcript in different organs of Arabidopsis, we conducted a RNA gel blot hybridization analysis using the 3'-specific cDNA probe of Athb-12. This probe does not contain the homeodomain and leucine zipper region. FIG. 4 shows that a single band of approximately 0.96 kb transcript is detected in mRNAs isolated from all organs such as root, stem, leaf and flower as well as seedling. The Athb-7 gene has also been reported to be expressed in all organs of plant (S öderman et al. 1994). The estimated size of the Athb-12 transcript closely agrees with the size of the Athb-12 cDNA.

Athb-7 mRNA is induced by environmental stress such as drought and exogenous abscisic acid (Söderman et al. 1996). Since the similar expression pattern and the high amino acid sequence homology between Athb-12 and Athb-7 have been observed, we tested whether Athb-12 is induced by water-stress (drought). Exposure to water-stress was done by removing the lid of the tissue culture plates and letting the plantlets to air-dry for the times indicated. The level of Athb-12 mRNA increased in response to water-stress under our experimental conditions (FIG. 5A). The higher level of accumulation was detected at 4 day treatment of air drying (FIG. 5A). When the plants were treated for 5 days of air drying, they were too dried to isolate RNA samples (not shown). The conditions of water-stress treatment were tested by reprobing the same RNA blots with a cDNA fragment derived from the Athb-7 gene, described as a drought-inducible gene, after removing the Athb-12 probe. The level of Athb-7 transcript also increased in response to these water-stress conditions (FIG. 5B). These results strongly suggest that the accumulation of Athb-12 mRNA is regulated by water status of the plant.

Many drought-inducible genes have been shown to be responsive to exogenous ABA (Merlot and Giraudat 1997; Bray et al. 1997). We examined the effect of exogenous ABA on the expression of Athb-12 by RNA gel blot analysis. The expression level of Athb-12 increased in response to exogenous ABA, as compared to the MS medium-treated control without ABA (FIG. 6A, lanes 1 and 4). We also examined the effects of other plant hormones, gibberellic acid (GA3), indole acetic acid (IAA) and cytokinin kinetin, on the expression of Athb-12. Treatment with these hormones did not result in a significant change in the expression level of Athb-12 under our experimental conditions (FIG. 6A, lanes 2, 3 and 5). The Athb-12 mRNA level also increased by the combination of ABA and GA3, but not by the combination of IAA and kinetin (FIG. 6A, lanes 6 and 7). To establish whether the concentrations and activities of the hormones are effective under our experimental conditions, the RNA gel blot was stripped and reprobed with a cDNA fragment derived from Athb-7 gene described as an ABA-inducible gene. As we expected, the Athb-7 transcript was induced by ABA but not by other hormones, consistent with that of Athb-12 (FIG. 6C).

We further examined the time course of accumulation of Athb-12 mRNA in response to exogenous ABA. The expression of Athb-12 transcript was strongly induced within 30 min after ABA treatment (FIG. 7A). The transcript level reached a maximum at 1 h and then gradually decreased until 24 h (FIG. 7A). To compare the time course of the Athb-12 and Athb-7 responses to ABA, the same RNA blots were reprobed with Athb-7 gene. The induction pattern of Athb-7 in response to ABA differed from that of Athb-12 (FIGS. 7A and B). A significantly increased level of Athb-7 mRNA was observed after 1 h of ABA treatment and reached a maximum at 4 h (FIG. 7B). These results suggest that both genes in response to ABA are regulated in different manners.

Taken together we propose that Athb-12 and Athb-7 proteins are involved in the plant's response to water-stress in different manners. Most of the homeobox genes identified in plants have been reported to be responsible for the development of plant. However, Athb-12 appears to be involved in environmental stress signalings such as water-stress. It can serve as a useful model system to study the functions of homeobox genes in the plant's responses to environmental stresses.

Dissection of Functional Domains of the Transcription Factor Athb-12

Homeodomain proteins are known as transcription factors to possess a transcriptional activation domain and a DNA binding domain (Gehring et al. 1994). Since Athb-12 has a homeodomain and leucine zipper motif in the N-terminal region, we tested whether the C-terminal region contains a transcriptional activation domain. The full-length (amino acids 1 to 235), N-terminal (amino acids 1 to 124) and C-terminal (amino acids 123 to 235) of Athb-12 was fused to 3' of the GAL4 DNA binding domain (Ma and Ptashne 1987), and the hybrid proteins were expressed in HF7C (Bartel et al. 1993). This strain has a GAL4 binding site cloned into the promoter region of a lacZ reporter gene. Thus, if the Athb-12 has a transcriptional activation domain that is functional in yeast, β-galactosidase will be induced. The full-length and C-terminal fusion constructs leaded to high-level transcription of the lacZ reporter gene but the N-terminal hybrid was not, indicating that the C-terminal region of Athb12 contains the transcriptional activation domain (FIG. 8). To dissect the transcriptional activation domain of Athb-12 in yeast, a series of C-terminal deletion hybrids were constructed and tested for the induction of the reporter gene. Deletion of amino acids N-terminal of the transcriptional activation domain eliminated the ability of the protein to activate the transcription of the lacZ reporter gene, whereas deletion of the amino acids N-terminal to the activation domain had no effect on transcriptional activation (FIG. 8). Thus, Athb-12 has a transcriptional activation domain, which is resided within amino acids 180–235.

DNA-protein Binding Assays

Figure 9:
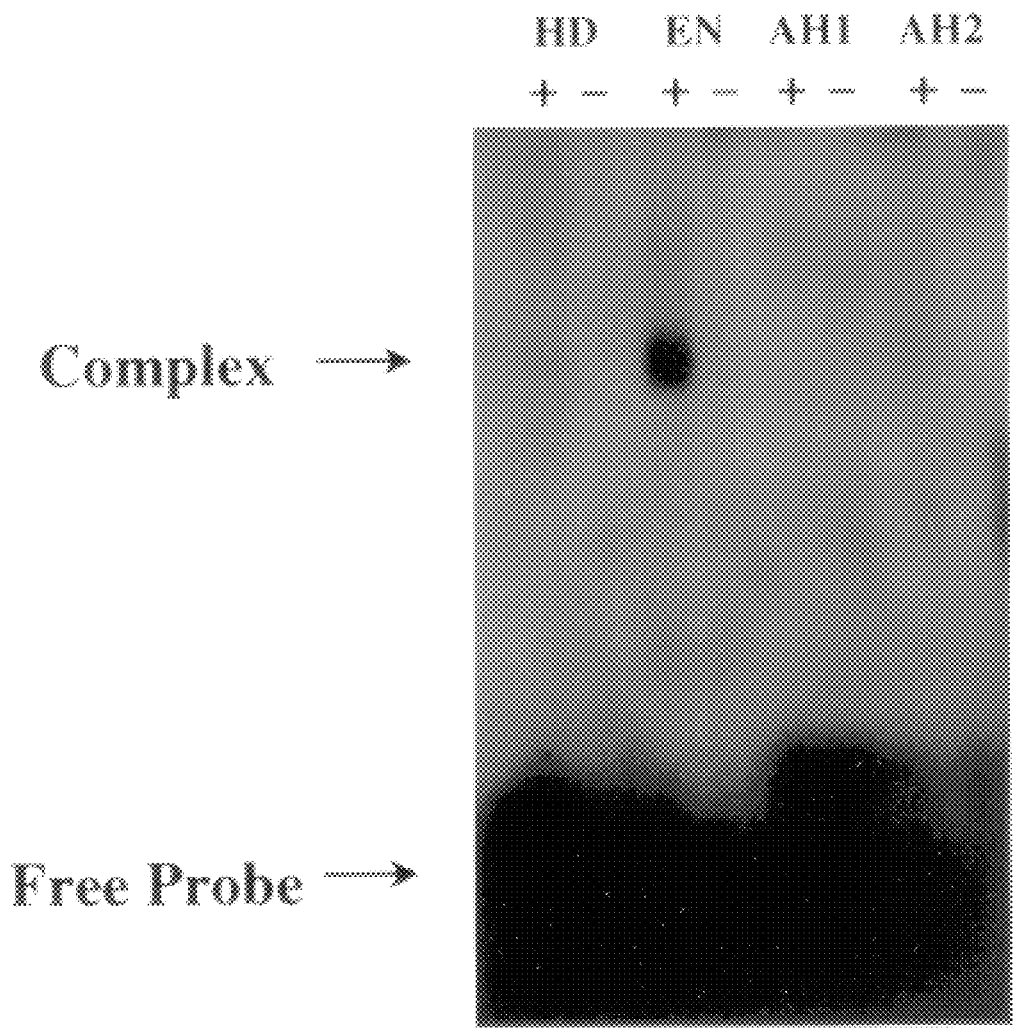
FIG. 9. Gel shift analysis. In vitro translation product containing full-length Athb-12 protein(+) was incubated with AH1, AH2, HD, or EN probe. The in vitro translation product without RNA prepared by in vitro transcription of the full-length Athb-12 construct was used as a negative control (−).

Since DNA-binding specificity is rather conserved among various HD proteins, we investigated whether Athb-12 interacts with known HD recognition sites, For this we used the 9 bp pseudopalindromic binding sites of the Arabidopsis Athb-1 and Athb-2 HD-Zip proteins, referred to as AH1 (CAAT(A/T)ATTG) and AH2 (CAAT(C/G)ATTG), respectively (Sessa et al. 1993). The combined sequences (HD; NAATNATTN) of AH1 and AH2 were also tested for the interaction with Athb-12. In addition, we tested the 12 bp palindromic sequence EN (TCAATTAATTGA), which is the consensus recognition site determined for Drosophila Engrailed and a number of other animal HD proteins (Desplan et al. 1988). The experiments were performed with in vitro translation product containing full-length Athb-12 protein. As shown in FIG. 9, Athb-12 protein was found to bind strongly to the EN binding site but showed no detectable interaction with the AH1 and AH2 binding sites. These results were further supported by the interaction test with HD, which was not interacted with Athb-12. None of the probes were bound by protein extract prepared by in vitro translation without RNA prepared by in vitro transcription of the full-length Athb-12 construct. These data suggest that the homeodomain of Athb-12 is a functional DNA-binding motif and also further support that Athb-12 is a transcription factor.

References

Bartel, P. L., Chien, C.-T., Sternglanz, R. and Fields, S. (1993) Elimination of false positives that arise in using the two-hybrid system. BioTechniques 14: 920–924.

Benson, D. A., Boguski, M. S., Lipman, D. J., and Ostell, J. (1997) GenBank. Nucleic Acids Res. 25: 1–6.

Blatt, M. R. and Thiel, G. (1993) Hormonal control of ion channel gating. Annu Rev Plant Physiol Plant Mol Biol 44: 543–567.

Boyer, J. S. (1982) Plant productivity and environment. Science 218: 443–448.

Bray, E. A. (1997) Plant responses to water deficit. Trends Plant Sci 2: 48–54.

Busch, S. J. and Sassone-Corsi, P. (1990) Dimers, leucine zippers and DNA-binding domains. Trends Genet 6: 36–40.

Carabelli, M., Sessa, G., Baima, S., Morelli, G. and Rubert, I. (1993) The Arabidopsis Athb-2 and -4 genes are strongly induced by far-red-rich light. Plant J 4: 469–479.

Chan, R. L. and Gonzalez, D, H. (1994) A cDNA encoding an HD-Zip protein from sunflower. Plant Physiol 106: 1687–1688.

De Robertis, E. M. (1994) The homeobox in cell differentiation and evolution. In Duboule, D. (ed), Guidebook to the Homeobox Genes, Oxford University Press, New York, pp. 11–23.

Desplan, C., Theis, J. and O'Farrell, P. H. (1988) The sequence specificity of homeodomain-DNA interaction. Cell 54: 1081–1090.

Gehring, W. J., Affolter, M. and Burglin, T. (1994) Homeodomain proteins. Annu. Rev. Biochem. 63: 487–526.

Gehring, W. J., Muller, M., Affolter, M., Percival-Smith, A., Billeter, M., Qian, Y. G., Otting, G. and Wuthrich, K. (1990) The structure of the homeodomain and its functional implication. Trends Genet 6: 323–329.

Ingram, J. and Bartels, D. (1996) The molecular basis of dehydration tolerance in plants. Annu Rev Plant Physiol Plant Mol Biol 47: 377–403.

Jaglo-Ottosen, K. R., Gilmour, S. J., Zarka, D. G., Schabenberger, O. and Thomashow, M. F. (1998) Arabidopsis CBF1 ever expression induces COR genes and enhances freezing tolerance. Science 280: 104–106.

Joshi, C. P. (1987) Putative polyadenylation signals in nuclear genes of higher plants: a compilation and analysis. Nucl Acids Res 15: 9627–9640.

Kawahara, R., Komamine, A. and Fukuda, H. (1995) Isolation and characterization of homeobox-containing genes of carrot. Plant Mol Biol 27: 155–164.

Lee, Y.-H and Chun, J.-Y. (1998) A new homeodomain-leucine zipper gene from *Arabidopsis thaliana* induced by water-stress and abscisic acid treatment. Plant Mol Biol 37: 377–384.

Lincoln, C., Long, J., Yamaguchi, J., Serikawa, K. and Hake, S. (1994) A knotted1-like homeobox gene in Arabidopsis is expressed in the vegetative meristem and dramatically alters leaf morphology when overexpressed in transgenic plant. Plant Cell 6: 1859–1876.

Lütcke, H. A., Chow, K. C., Mickel, F. S., Moss, K. A., Kern, H. F. and Scheele, G. A. (1987) Selection of AUG initiation codons differs in plants and animals. EMBO J 6: 43–48.

Ma, J. and Ptashne, M. (1987) Deletion analysis of GAL4 defines two transcriptional activating segments. Cell 48: 847–853.

Mattsson, J., Söderman, E., Svenson, M., Borkird, C. and Engström, P. (1992) A new homeobox-leucine zipper gene from *Arabidopsis thaliana*. Plant Mol Biol 18: 1019–1022.

McCue, K. F. and Hanson, A. D. (1990) Drought and salt tolerance: towards understanding and application. Trends Biotechnol. 8: 358–362.

McGinnis, W. and Krumlauf, R. (1992) Homeobox genes and axial patterning. Cell 68: 283–302.

Meijer, A. H., Scarpella, E., van Dijk, E. L., Qin, L., Taal, A. J. C., Rueb, S., Harrington, S. E., McCouch, S. R., Schilperoort, R. A. and Hoge, J. H. C. (1997) Transcriptional repression by Oshox1, a novel homeodomain leucine zipper protein from rice. Plant J 11: 263–276.

Meissner, R. and Theres, K. (1995) Isolation and characterization of the tomato homeobox gene THOM1. Planta 195: 541–547.

Merlot, S. and Giraudat, J. (1997) Genetic analysis of abscisic acid signal transduction. Plant Physiol 114: 751–757.

Moon, Y. H., Choi, D. S., Kim, J. C., Han, T. J., Cho, S. H., Kim, W. T. and Lee, K. W. (1996) Isolation and characterization of a homeodomain-leucine zipper gene, Gmh1, from soybean somatic embryo. Mol Cells 6: 366–373.

Murashige T., Skoog F: A revised medium for rapid growth and bioassays with tobacco tissue cultures. Physiol Plant 15: 473–497 (1962).

Newman, T., de Bruijin, F. J., Green, P., Keegstra, K., Kende, H., McIntosh, L., Ohlrogge, J., Raikhel, N., Somerville, S., Thomashow, M., Retzel, E. and Somerville, C. (1994) Genes galore: a summary of methods for accessing results from large-scale partial sequencing of anonymous Arabidopsis cDNA clones. Plant Physiol 106: 1241–1255.

Ruberti, I., Sessa, G., Lucchetti, S. and Morelli, G. (1991) A novel class of plant proteins containing a homeodomain with a closely linked leucine zipper motif. EMBO J 10: 1787–1791.

Sambrook, J., Fritsch, E. F., and Maniatis, T. (1989) Molecular Cloning: A Laboratory Manual. Cold Spring Harbor Laboratory Press, Cold Spring Harbor, N.Y.

Schena, M. and Davis, R. W. (1992) HD-Zip proteins: Members of an Arabidopsis homeodomain protein superfamily. Proc Natl Acad Sci USA 89: 3894–3898.

Scott, M. P., Tamkun, J. W. and Hartzell III, G. W. (1989) The structure and function of the homeodomain. Biochim Biophys Acta Rev Cancer 989: 25–48.

Sessa, G., Carabelli, M., Ruberti, L., Lucchetti, S., Beima, S. and Morelli, G. (1994) Identification of distinct families of HD-ZIP proteins in *Arabidopsis thaliana*. In: Puigdomenech P, Coruzzi G (eds), Molecular Genetic Analysis of Plant Development and Metabolism Berlin, Springer Verlag, pp. 411426.

Sessa, G., Morelli, G. and Ruberti, I. (1993) The Athb-1 and -2 HD-Zip domains homodimerize forming complexes of different DNA binding specificities. EMBO J. 12: 3507–3517.

Shinozaki, K. and Yamaguchi-Shinozaki, K. (1997) Gene expression and signal transduction in water-stress response. Plant Physiol 115: 327–334.

Söderman, E., Mattsson, J. and Engström, P. (1996) The Arabidopsis homeobox gene ATHB-7 is induced by water deficit and by abscisic acid. Plant J 10: 375–381.

Söderman, E., Mattsson, J., Svenson, M., Borkird, C. and Engström, P. (1994) Expression patterns of novel genes encoding homeodomain leucine-zipper proteins in *Arabidopsis thaliana*. Plant Mol Biol 26: 145–154.

Ward, J. M., Pei, Z.-M. and Schroeder, J. I. (1995) Roles of ion channels in initiation of signal transduction in higher plants. Plant Cell 7: 833–844.

What is claimed is:

1. An isolated nucleic acid molecule encoding the transcription factor Athb-12.

2. The isolated nucleic acid molecule of claim 1, wherein the nucleic acid molecule is a messenger RNA molecule.

3. The isolated nucleic acid molecule of claim 1, wherein the nucleic acid molecule is a DNA molecule.

4. The DNA molecule of claim 3, wherein the DNA molecule is a cDNA molecule.

5. The cDNA molecule of claim 4 comprising the nucleotide sequence shown in FIG. 1 (SEQ ID No. 1).

* * * * *

SEQUENCE LISTING

<160> NUMBER OF SEQ ID NOS: 2

<210> SEQ ID NO 1
<211> LENGTH: 965
<212> TYPE: DNA
<213> ORGANISM: Arabidopsis thaliana

```
<400> SEQUENCE: 1
ggcacgagcc ttctctctta atcaaaatca agaaacttac aagatctggt gaaaaccatg      60
gaagaaggag attttttcaa ctgctgtttc agcgagatta gtagtggcat gaccatgaat     120
aagaagaaga tgaagaagag caataaccaa aagaggttta cgaggaaca gatcaagtca     180 cttgagctta tatttgagtc tgagacgagg cttgagccga ggaagaaggt tcaggtagct     240
agagagctag ggctgcaacc aagacaaatg actatatggt ttcaaaaaaa gagggctcga     300
tggaaaacta agcaacttga gaaagagtat aacactctta gagccaatta caacaatttg     360
gcttcacaat ttgaaatcat gaagaaagaa agcaatctc tggtctctga gctgcagaga     420
ctaaacgaag agatgcaaag gcctaaagaa gaaaagcatc atgagtgttg tggtgatcaa     480
ggactggctc taagcagcag cacagagtcg cataatggaa agagtgagcc agaagggagg     540
ttagaccaag ggagtgttct atgtaatgat ggtgattaca caacaacat taaaacagag     600 tattttaggg tccagggaga gactgatcat gagctgatga acattgtgga gaaagctgat     660
gatagttgct tgacatcttc tgagaattgg ggaggtttca attctgattc tctcttagac     720
caatctagca gcaattaccc taactggtgg gagttttggt cataaaagca tataagaaaa     780
aaacagaaca taagcgaaga gaaagagtgt gaatagtttg taaattatgt gttaagaaaa     840
taaatttagt ttagtttaaa tcttgtttcg atctatgtat ctactatgtt caatactctt     900
tgtagctaat tagtagctta taatgagact agaaaagttt tgaagtcaaa aaaaaaaaa     960 aaaaa                                                                 965

<210> SEQ ID NO 2
<211> LENGTH: 235
<212> TYPE: PRT
<213> ORGANISM: Arabidopsis thaliana

<400> SEQUENCE: 2

Met Glu Glu Gly Asp Phe Phe Asn Cys Cys Phe Ser Glu Ile Ser Ser
              5                  10                  15

Gly Met Thr Met Asn Lys Lys Met Lys Lys Ser Asn Asn Gln Lys
         20                  25                  30

Arg Phe Asn Glu Glu Gln Ile Lys Ser Leu Glu Leu Ile Phe Glu Ser
         35                  40                  45

Glu Thr Arg Leu Glu Pro Arg Lys Lys Val Gln Val Ala Arg Glu Leu
     50                  55                  60

Gly Leu Gln Pro Arg Gln Met Thr Ile Trp Phe Gln Asn Lys Arg Ala
 65                  70                  75                  80

Arg Trp Lys Thr Lys Gln Leu Glu Lys Glu Tyr Asn Thr Leu Arg Ala
                 85                  90                  95

Asn Tyr Asn Asn Leu Ala Ser Gln Phe Glu Ile Met Lys Lys Glu Lys
            100                 105                 110

Gln Ser Leu Val Ser Glu Leu Gln Arg Leu Asn Glu Glu Met Gln Arg
        115                 120                 125

Pro Lys Glu Glu Lys His His Glu Cys Cys Gly Asp Gln Gly Leu Ala
    130                 135                 140

Leu Ser Ser Ser Thr Glu Ser His Asn Gly Lys Ser Glu Pro Glu Gly
145                 150                 155                 160

Arg Leu Asp Gln Gly Ser Val Leu Cys Asn Asp Gly Asp Tyr Asn Asn
                165                 170                 175

Asn Ile Lys Thr Glu Tyr Phe Arg Val Gln Gly Glu Thr Asp His Glu
            180                 185                 190
```

-continued

```
Leu Met Asn Ile Val Glu Lys Ala Asp Asp Ser Cys Leu Thr Ser Ser
        195                 200                 205

Glu Asn Trp Gly Gly Phe Asn Ser Asp Ser Leu Leu Asp Gln Ser Ser
    210                 215                 220

Ser Asn Tyr Pro Asn Trp Trp Glu Phe Trp Ser
225                 230                 235
```